United States Patent [19]

Rosenberg

[11] 4,013,071
[45] Mar. 22, 1977

[54] FASTENERS PARTICULARLY USEFUL AS ORTHOPEDIC SCREWS

[76] Inventor: Lior Rosenberg, 4 Ophir St., Tel Aviv, Israel

[22] Filed: Nov. 11, 1975

[21] Appl. No.: 631,137

[30] Foreign Application Priority Data

Nov. 11, 1974 Israel .................................. 46030

[52] U.S. Cl. .............................. 128/92 B; 85/75; 85/83; 3/1.9
[51] Int. Cl.² ..................... A61B 17/18; A61F 5/04
[58] Field of Search ........... 128/92 R, 92 B, 92 BA, 128/92 BB, 92 BC, 92 C; 3/1, 1.9–1.913; 32/10 A; 85/83, 84, 75

[56] References Cited

UNITED STATES PATENTS

| | | | |
|---|---|---|---|
| 2,397,545 | 4/1946 | Hardinge | 128/92 B |
| 2,490,364 | 12/1949 | Livingston | 128/92 BB |
| 3,708,883 | 1/1973 | Flander | 32/10 A |

FOREIGN PATENTS OR APPLICATIONS

| | | | |
|---|---|---|---|
| 739,089 | 10/1932 | France | 85/83 |
| 193,876 | 2/1938 | Switzerland | 85/83 |

*Primary Examiner*—Ronald L. Frinks
*Attorney, Agent, or Firm*—Benjamin J. Barish

[57] ABSTRACT

Fasteners particularly useful as orthopedic screws comprise an external fastening member having a shank formed with a head at one end, external spiral threads extending to the opposite end, an internal bore extending axially through the head of the shank, and a plurality of side slits formed radially through the tip at the opposite end of the shank to the bore to provide a plurality of outwardly expansible tips at the latter end. The fastener also includes, an internal spreading member axially movable within the bore to engage the tips of the fastening member and thereby to outwardly spread them.

In one described embodiment, the fastener further includes an insert removably received between heads on the two members such that when the insert is in position, the internal spreading member or the insert may be rotated to rotate the external fastening member in the fastening direction and when the insert is removed, the internal spreading member may be rotated to expand the tips of the external member. In a second described embodiment, the internal spreading member includes a lower enlarged end which is axially movable to expand the tips of the external fastening member.

4 Claims, 8 Drawing Figures

FASTENERS PARTICULARLY USEFUL AS ORTHOPEDIC SCREWS

BACKGROUND OF THE INVENTION

The present invention relates to fasteners, and particularly to fasteners useful in orthopedic surgery.

Various types of orthopedic fasteners, particularly screws, are commonly used in orthopedic surgery for connecting or strengthening fractured bones, joints, implants and the like. Such fasteners are usually made of special alloys of stainless steel, but are otherwise generally similar to the conventional fasteners used in other fields.

An object of the present invention is to provide novel fasteners which effect a firmer grip between the members being fastened, this being very important in orthopedic surgery where frequently there is a critical limitation as to the size of fastener that may be used. Another object of the invention is to provide novel fasteners which may be applied in a simple and convenient manner, this also being very important in orthopedic surgery because of the operating conditions under which such surgery is performed.

SUMMARY OF THE INVENTION

According to a broad aspect of the present invention, there is provided a fastener, particularly useful in orthopedic surgery comprising an external fastening member and an internal spreading member. The external fastening member includes a shank formed with a head at one end, external spiral threads, an internal bore extending axially through the head and at least partly through the shank towards its opposite end, and a plurality of side slits formed radially through the opposite end of the shank to the bore to provide a plurality of outwardly expansible tips at the opposite end. The internal spreading member is receivable within the bore and is axially movable therein to engage the tips of the fastening member and thereby to spread them outwardly.

Two preferred embodiments of the invention are described below for purposes of example. In one described embodiment, the upper end of the internal spreading member is also formed with a head, and its lower end is movable towards the expansible tips of the external fastening member in order to expand them. In this described embodiment, an insert is provided between the heads of the two members, which insert is used to cause the rotational movement of the internal member also to rotate the external member in the fastening direction, the insert being removable to permit the internal member to be further rotated and thereby to move axially of the external member and to expand its tips.

In a described variation of this embodiment, the insert may also be used for rotating the external fastening member when the latter is threaded into the object (e.g. bone) to which it is fastened. In this variation, the insert is of polygonal shape to facilitate its being gripped by a rotating tool, such as a wrench, and it includes a projection at its underside receivable within a recess in the upper face of the head of the external fastening member, so that the rotation of the insert by the rotating tool will also effect a rotation of the external fastening member.

In a second described embodiment, the internal spreading member is movable in the opposite direction, i.e., its lower end is moved towards the head of the external member, in order to expand the tips of the external member. In this embodiment, the internal member is formed with an enlarged lower end which is engagable with the expansible tips of the external member to expand them upon the axial movement of the internal member towards the head of the external member. In this described embodiment, the lower enlarged end of the internal spreading member is further formed with a plurality of vanes receivable in the slits of the external fastening member for preventing the rotation of the internal member relative to the external one.

In both of the described embodiments, the fastener is conveniently manipulated and provides a very strong fastening action, advantages which are particularly important in enabling their use in orthopedic surgery.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
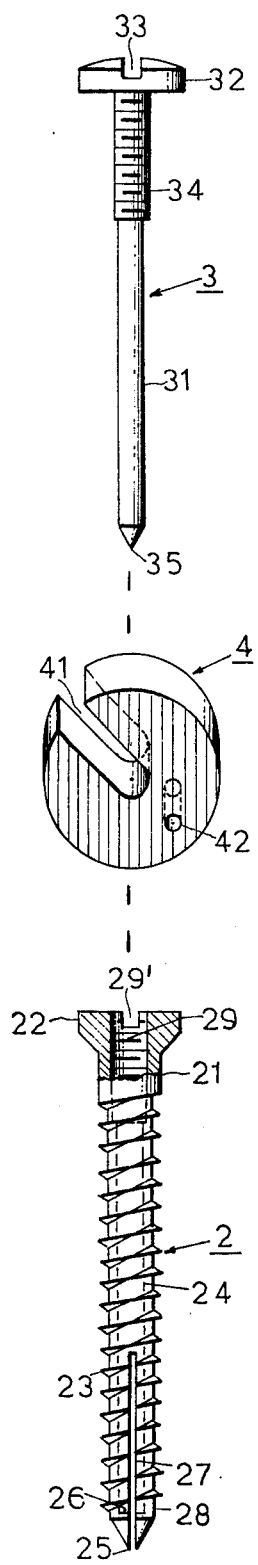
FIGS. 1–4 illustrate one preferred embodiment of the invention, FIG. 1 showing the main elements of the fastener of this embodiment, and FIGS. 2–4 showing different stages of its application.

With reference first to the embodiment of the invention illustrated in FIGS. 1–4, it will be seen that this embodiment includes three main parts, namely an external rod-shaped member generally designated 2, an internal rod-shaped member generally designated 3, and an insert generally designated 4 adapted to be inserted and then removed from between the two members.

The external rod-shaped member 2 is a fastening member. It comprises a shank 21 formed with a head 22 at one end, external threads 23 at the opposite end, and internal bore 24 extending axially through the head of the shank 2 towards its opposite end 25 but terminating just short of its opposite end as shown at 26 in FIG. 4, and a plurality of side slits 27 formed radially through the opposite end of the shank to merge with its internal bore 24. The side splits 27 thereby produce a plurality of outwardly expansible tips 28 at the threaded end 23 of the member opposite to its head 22. The upper end of bore 24 passing through head 22 is internally threaded as shown at 29, and the head 22 is formed with a tool-receiving (.e.g. screw-driver) notch as shown at 29'.

The internal rod-shaped member 3 is a spreading member. It is formed with a shank 31, a head 32 including a notch 33 for an applicator tool (e.g. screw driver 50, FIGS. 2–4), external spiral threads 34 at the head end of shank 31, and a rounded or pointed tip 35 at the opposite end of the shank.

Insert member 4 is of disc-shape and is formed with a side slot 41 of substantially the same diameter as the threaded shank portion 34 of the internal spreading member 3, slot 41 extending from one edge of the insert to about its center. This insert is further formed with an opening 42 laterally of and in line with slot 41.

Figure 2:
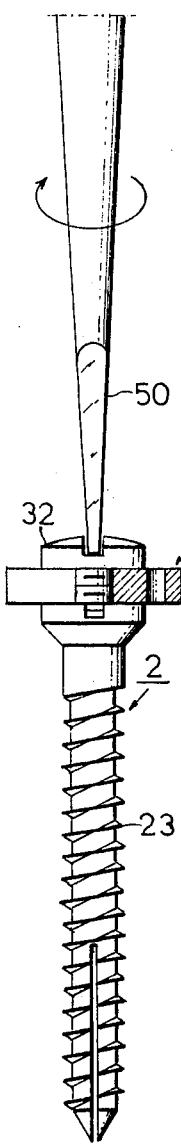
Figure 3:
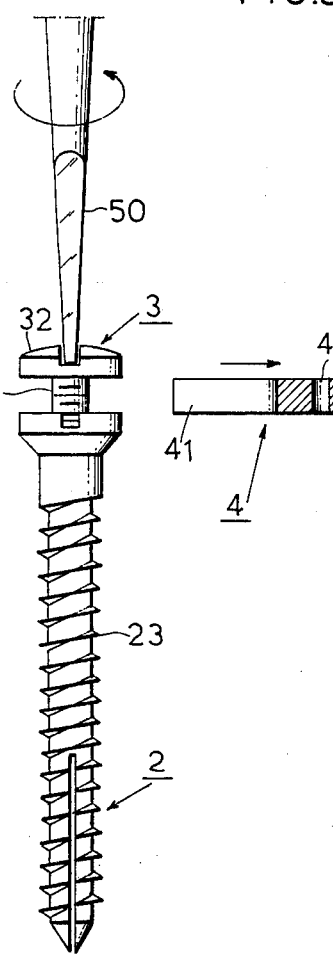
Figure 4:
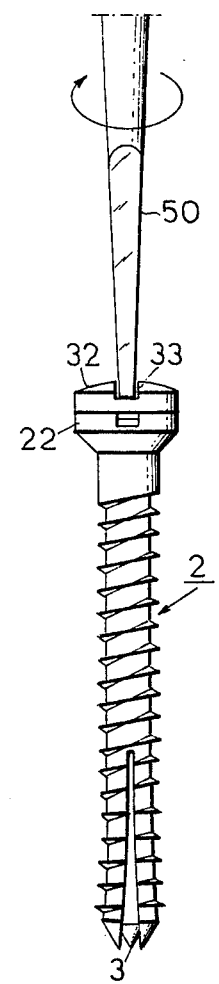

FIGS. 2–4 illustrate the manner of using the fastener of FIG. 1. When applying the fastener, the internal spreading member 3 is passed through bore 24 of the external fastening member 2, with insert 4 interposed between the heads 32, 22 of the two members. The internal member 3 is then threaded into the external member 2, for example by the use of a screw-driver 50 received in notch 33 of the internal member. The internal member is threaded by rotating screw-driver 50 in the direction of the threads (i.e. clockwise, FIG. 2) until insert 4 is engaged by the lower surface of head 32 of the internal member 3 and the upper surface of head 22 of the external member 32. The spiral threads 34 on the internal member 3 run in the same direction as spiral thread 23 on the external member 2, so that further rotation of the screw-driver will cause the external member 2 also to rotate (in the fastening direction) with internal member 3, the coupling between the two members being effected by their contact with insert 4.

When the external member 2 has been sufficiently threaded into the object (e.g. bone,) receiving the fastener, the screw-driver is rotated slightly in the opposite direction (i.e., counter-clockwise as shown in FIG. 3) in order to unthread the internal member 3 slightly so as to release the insert 4. The insert may then be removed from between the heads of the two members by applying a sidewise movement to the insert. Its opening 42 facilitates the removal of the insert, this opening being usable for receiving a tool to apply the side movement, or for receiving a thread to be pulled in order to remove the insert.

After insert 4 has been removed, the internal member 3 is then rotated in the original, (i.e. clockwise, FIG. 4) direction. This causes the tip 35 of its shank 31 to move towards the tip 25 of the external fastening member 2, until tip 35 of member 3 engages the end 26 of bore 24, at which time it spreads the tips 28 outwardly, thereby firmly anchoring the fastener within the object receiving it.

If it is desired to remove the fastener, the internal member 3 is first removed by applying a screw-driver to its notch 33 and rotating same in the reverse direction. This releases the spreaded tips 28 of the external fastening member 2. Notch 29' of the latter member is then used, by applying the screw-driver thereto, for unthreading the fastening member from the object.

Figure 5:
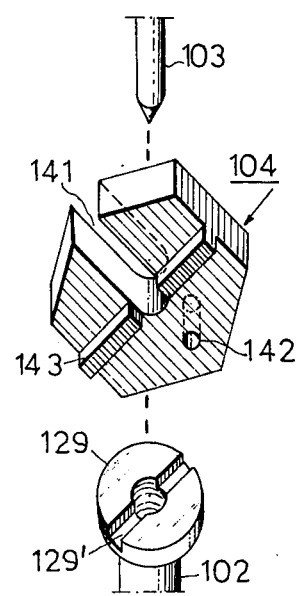
FIG. 5 illustrates a variation in the fastener of FIGS. 1–4.

FIG. 5 illustrates a variation wherein the insert, therein designated 104 may also be used for threading the fastener into the object. In this case, the insert 104 is of polygonal (e.g. hexagonal) shape to facilitate its being gripped by a rotating tool, such as a wrench. The insert is also formed with the side slot 141 for receiving the internal spreading member 103, and also with the aperture 142, these elements corresponding to elements 41 and 42 in the FIGS. 1–4 embodiment. In this case, however, the insert is further formed with a lower rib or projection 143 engagable with notch 129; formed in head 129 of the external fastening member 102, so that rotation of the insert 104 also rotates the external fastening member 102.

Figure 6:
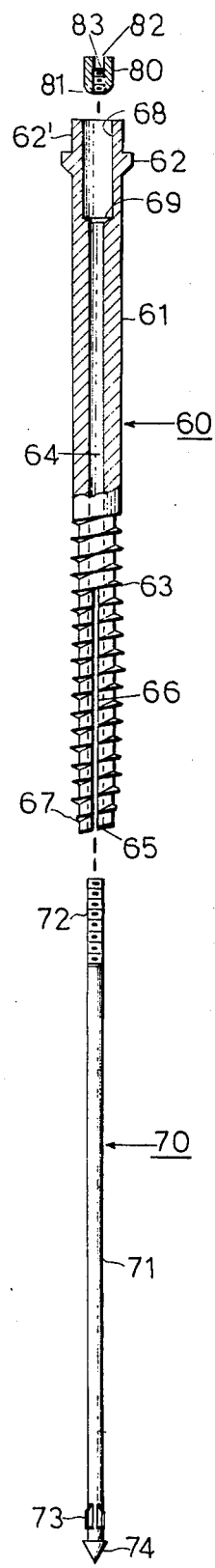
FIGS. 6–8 illustrate a fastener constructed in accordance with a second embodiment of the invention, FIG. 6 showing the main elements of this fastener, and FIGS. 7 and 8 showing different stages in its application.
Figure 7:
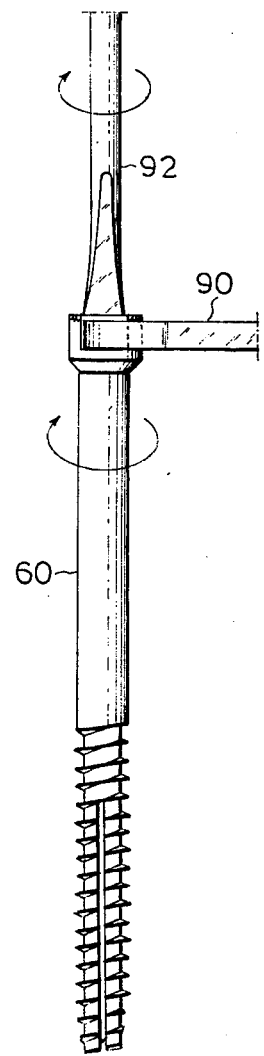
Figure 8:
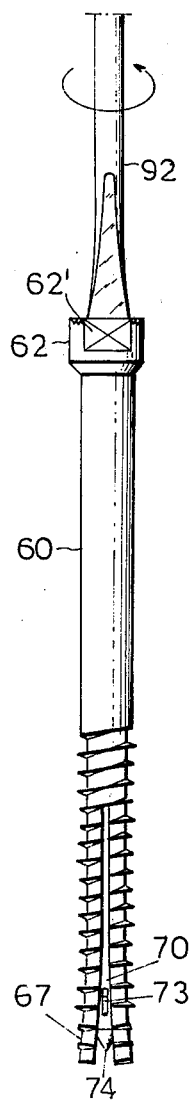

FIGS. 6–8 illustrates a second embodiment of the invention particularly useful for larger fasteners. This embodiment includes two main members, namely an external rod-shaped fastening member generally designated 60, and an internal rod-shaped spreading member generally designated 70. It further includes a nut 80 receivable within the upper end of the external fastening member 60 for moving the internal spreading member 70, as will be described more fully below.

The external fastening member 60 includes a shank 61 formed with a head 62 at one end, external spiral threads 63 at the opposite end, an internal bore 64 extending axially through the head and completely through the shank to its opposite end 65, and three side slits 66 formed radially through the lower end of the shank to the internal bore to provide three outwardly expansible tips 67. It is to be noted that whereas in the FIGS. 1–5 embodiment the bore (therein 24) terminates short of the threaded tip (therein 25) of the external fastening member, in the embodiment of FIGS. 6–8 the bore 64 extends completely through the shank of the external fastening member from its head 62 through its threaded tip 65.

Head 62 of member 60 is formed with a tool-engaging notch 62'. In addition the portion of bore 64 within head 62 is enlarged, as shown at 68, to define a shoulder 69 at its juncture with the remainder of bore 64.

The internal spreading member 70 is formed with a shank 71 of smaller diameter than of the main portion of bore 64. The upper end of shank 71 is unheaded but is formed with external spiral threads 72. The lower end of the shank is provided with a plurality (e.g. 3) radial vanes 73, and terminates in an enlarged end 74 of larger external diameter than that of the vanes 73.

Nut 80 is received within the enlarged portion 68 of bore 61, and is formed with a lower rounded tip 81 engagable with shoulder 69. This nut is internally threaded, as shown at 82, and is formed with a transverse notch 83 for engagement by a tool (such as a driver 92 in FIG. 8).

In use, the internal spreading member 70 is disposed wholly within the bore 64 of the external fastening member 60, with the upper end of member 70 threaded within nut 80. The fastening member (together with the spreading member 70 and nut 80 within it) is then threaded into the object (e.g., bone) by means of a wrench, such as shown at 90 in FIG. 7, engaging the notched sides 62' of the fastening member head 62. When the fastening member is threaded to the proper depth, tool 90 is removed. Another tool 92 (FIG. 8) is then applied to nut 80 within the enlarged bore portion 68 of the fastening member 60, and is used for rotating the nut. Since the lower surface 81 of the nut limits against shoulder 69 of the fastening member, the internal spreading member 70 is moved upwardly within the fastening member, causing the enlarged end 74 of the spreading member to engage the tips 67 of the fastening member and to spread them outwardly. During this upward movement of the internal spreading member 70 with respect to the external fastening member 60, vanes 73 move within slots 66 thereby guiding the internal member and preventing its rotation with respect to the external member which is already firmly fastened. When the lower tips 67 of the fastening member have been outwardly spread in the above described manner, tool 92 may then be removed, but nut 80 is retained in place.

In order to remove the fastener, nut 80 is rotated in the reverse direction to move the internal spreading member 70 downwardly, thereby causing the tips 67 of the external member to return to their normal closed positions. The external member may then be unthreaded by rotating same in the direction opposite to that in which they were threaded.

While the invention has been described with reference to fasteners for use in orthopedic surgery, it will be appreciated that such fasteners, or features thereof, could advantageously be used in many other applications as well.

What is claimed is:

1. A fastener particularly useful in orthopedic surgery, comprising: an external fastening member having a shank formed with a head at one end, external spiral threads, an internal bore extending axially through the head and at least partly through the shank towards its opposite end, internal threads adjacent to its head and a plurality of side slits formed radially through said opposite end of the shank to said bore to provide a plurality of outwardly expansible tips at said opposite end; an internal spreading member receivable within said bore and being formed with a head and external threads in the same direction as the external threads of the external fastening member; and an insert removably received between the heads of the fastening and spreading members such that when the insert is in position between the two heads and engages them on its opposite faces, the spreading member may be rotated to transmit its rotation to the fastening member in the threading direction, and when the insert is removed, the spreading member may be further rotated to cause it to move axially within the bore of the fastening member and thereby to spread its tips outwardly.

2. A fastener according to claim 1, wherein said insert is of disc-shape and is formed with a side slot extending from one edge thereof, said slot having a width at least equal to the diameter of the internal spreading member to permit the insert to be readily removed sidewise from the two members while the spreading member is still threaded in the bore of the fastening member.

3. A fastener according to claim 2, wherein said insert further includes an opening aligned with said slot to facilitate removal of the insert by applying a side force thereto while the insert is in position between the heads of the fastening and spreading members.

4. A fastener according to claim 2, wherein said insert is of polygonal shape to facilitate its being gripped by a rotating tool, and includes a projection at the underside thereof receivable within a recess in the upper face of the head of the external fastening member to effect the rotation thereof upon the rotation of the insert by the rotating tool.

* * * * *